US008017121B2

(12) United States Patent
Kishimoto et al.

(10) Patent No.: US 8,017,121 B2
(45) Date of Patent: *Sep. 13, 2011

(54) CHRONIC RHEUMATOID ARTHRITIS THERAPY CONTAINING IL-6 ANTAGONIST AS EFFECTIVE COMPONENT

(75) Inventors: Tadamitsu Kishimoto, Tondabayashi (JP); Masahiko Mihara, Gotenba (JP); Yoichiro Moriya, Gotenba (JP); Yoshiyuki Ohsugi, Gotenba (JP)

(73) Assignees: Chugai Seiyaku Kabushika Kaisha, Tokyo (JP); Tadamistu Kishimoto, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/756,125

(22) Filed: Jan. 9, 2001

(65) Prior Publication Data

US 2001/0001663 A1    May 24, 2001

Related U.S. Application Data

(60) Division of application No. 09/233,474, filed on Jan. 20, 1999, which is a division of application No. 08/817,084, filed as application No. PCT/JP95/01144 on Jun. 7, 1995, now Pat. No. 5,888,510, and a continuation-in-part of application No. 08/971,997, filed on Feb. 21, 1997, now abandoned, which is a continuation of application No. 08/268,520, filed on Jun. 30, 1994, now abandoned.

(30) Foreign Application Priority Data

Oct. 7, 1994   (JP) ..................... 6-244035

(51) Int. Cl.
    A61K 39/395    (2006.01)
(52) U.S. Cl. .................. 424/145.1; 424/158.1
(58) Field of Classification Search .......... 424/133.1, 424/141.1, 152.1, 810; 514/825; 530/387.3, 530/388.1, 388.2
    See application file for complete search history.

(56) References Cited

U.S. PATENT DOCUMENTS

| 5,210,075 | A | 5/1993 | Scholz et al. ............... 514/14 |
| 5,559,012 | A | 9/1996 | Brailly et al. ............ 435/70.21 |
| 5,591,827 | A | 1/1997 | Brakenhoff et al. .......... 530/351 |
| 5,670,373 | A | 9/1997 | Kishimoto |
| 5,851,793 | A | 12/1998 | Kishimoto |
| 5,888,510 | A | 3/1999 | Kishimoto et al. ........ 424/141.1 |
| 6,428,979 | B1 | 8/2002 | Kishimoto |
| 6,723,319 | B1 | 4/2004 | Ito et al. |
| 2002/0187150 | A1 | 12/2002 | Mihara et al. |
| 2003/0236260 | A1 | 12/2003 | Shimojo et al. |
| 2004/0115197 | A1 | 6/2004 | Yoshizaki et al. |
| 2006/0292147 | A1 | 12/2006 | Yoshizaki et al. |

FOREIGN PATENT DOCUMENTS

| CA | 2031455 A1 | 6/1992 |
| DE | 39 39 706 | 3/1991 |
| EP | 0 381 168 A | 8/1990 |
| EP | 0 399 429 | 11/1990 |
| EP | 0 409 607 | 1/1991 |
| EP | 0 572 118 | 12/1993 |
| EP | 0 617 126 | 9/1994 |
| EP | 0 628 639 | 12/1994 |
| EP | 0 791 359 A1 | 8/1997 |
| FR | 2 694 767 | 2/1994 |
| JP | 3-291236 | 4/1990 |
| JP | 4-89433 | 7/1990 |
| JP | 04-187645 A | 7/1992 |
| WO | 91/07986 | 6/1991 |
| WO | 92/19759 | 11/1992 |
| WO | WO 2004/096273 A1 | 11/2004 |

OTHER PUBLICATIONS

Bendig, M Methods: Companion to Methods in Enzymology 8 pp. 83-93, 1995.*
Hirano et al., "Biological and clinical aspects of interleukin 6," Immunology Today, 1990, 11(12):443-449.
Sipe et al., "Cytokine reduction in the treatment of joint conditions," Mediators of Inflammation, 1994, 3:243-256.
Harigai et al., Rheumatoid Adherent Synovial Cells Produced B Cell Differentiation Factor Activity Neutralizable by Antibody to B Cell Stimulatory Factor-2/Interleukin 6. The Journal of Rhematology, pp. 1616-1622, (1988).
Matsuda et al., "Establishment of An Interleukin 6 (IL-6)/B Cell Stimulatory Factor 2-dependent Cell Line And Preparation of Anti-Il 6 Monoclonal Antibodies", Eur. J. Immunol., vol. 18. pp. 951-956, (1988) VCH Verlagsgesellschaft mbH, D-6940 Weinheim, 1988.
Hirata et al., "Characterization of IL-6 Receptor Expression by Monoclonal and Polycholan Antibodies", The Journal of Immunology, vol. 143, pp. 2900-2906, (1989).
Hirano et al., "Excessive Production of Interleukin 6/B Cell Stimulatory Factor-2 in rheumatoid Arthritis", Eur. J. Immunol. 18, pp. 1797-1801. (1988), VCH Verlagsgesellschaft mbH, D-6940 Weinheim, 1988.
Houssiau, et al., "Interleukin-6 in Synolvial Fluid and Serum of Patients with Rheumatoid Arthritis and Other Inflammatory Arthritis", Arthritis and Rheumatism 31, pp. 784-788, (1988).
Waage et al., Interleukin-6 Synovial Fluid from Patients with Arthritis, Clinical Immunology and Immunopatholog 50, pp. 394-398, (1989), 1989 Academic Press, Inc.
Bhardwaj et al., "IL-6/IFN-$\beta_2$ In Synovial Effusions of Patient s with Rheumatoid Arthritis and Other Arthritides", J. of Immunology 143, pp. 2153-2159, (1989), 1989 The American Association of Immunologists.
Aderka et al. "Il-6 Inhibits Lipopolysaccharide-induced Tumor Necrosis Factor Production in Cultured Human Monocytes U937 Cells, and In Mice", J of Immunology 143, pp. 3517-3523, (1989)., 1989 The American Association of Immunologists.

(Continued)

Primary Examiner — Gerald R Ewoldt
(74) Attorney, Agent, or Firm — Foley & Lardner LLP

(57) ABSTRACT

There is provided a synovial cell growth inhibitor, or a pharmaceutical composition for treatment of chronic rheumatoid arthritis based on the synovial cell growth inhibitor.
The pharmaceutical composition for treatment of chronic rheumatoid arthritis or synovial cell growth inhibitor contains an IL-6 antagonist, such as IL-6 antibody or IL-6R antibody, as an effective component.

3 Claims, 6 Drawing Sheets

OTHER PUBLICATIONS

Schindler et al., "Correlations and Interactions in the Production of Interleukin-6 (IL-6), IL-1, and Tumor Necrosis Factor (TNF) in Human Blood Mononuclear Cells: IL-6 suppresses IL-1 and TNF", *Blood 75*, pp. 40-47, (1990), 1990 The American Society of Mehatology.

Saito et al., "Preparation of Soluble Murine Il-6 Receptor and Anti-Murine Il-6 Receptor Antibodies", *The Journal of Immunology* 147, pp. 168-173, (1991), 1991 The American Association of Immunologists.

Yasukawa et al., "Inhibitors of Interleukin-6", *Toso Kenkyu Hokoku* (32(20), pp. 77-91, Abstract, (1991).

Mihara et al., "Interleukin 6 Inhibits Delayed-Type Hypersensitivity and the Development of Adjuvant Arthritis", *Eur. J. Immunol. 21*, pp. 2327-2331. (1991).

Heremans et al., "Protective Effect Of Anti-Interleukin-6 Antibody Against Endotoxin, Associated with Paradoxica Increased IL-6 Levels", *Eur. J. Immunol. 22*, pp. 2395-2401, (1992), VCH Verlagsgesellschaft mbH, D-6940 Weinheim, 1992.

Wendling et al., "Treatment of Severe Rheumatoid Arthritis by Anti-Interleukin 6 Monoclonal Antibody", *J. of Rheumatology 20*. pp. 259-262, (1993).

Sack et al., "Interleukin-6 In Synovial Fluid is Closely Associated with Chronic Synovitis in Rheumatoid Arthritis" *Rheumatol. Int. 13*, pp. 45-51, (1993).

Madhok et al., "Serum Interleukin-6 Levels in Rheumatoid Arthritis: Correlations with Clinical and Laboratory Indices of Disease Activity", *Annals of the Rheumatic Diseases 52*, pp. 232-234, (1993).

Tilg et al., Interleukin-6 (IL-6) as an Anti-inflammatory Cytokine: Induction of Circulating IL-1 Receptor Antagon and Soluble Tumor Necrosis Factor Receptor p55, *Blood 83*, pp. 113-118, (1994), 1994 The American Society of Hematology.

Punzi et al., "Interrelationship Between Synovial Fluid Interleukin (IL)-6, Il-1β and Disease Activity Indices in Rheumatoid Arthritis", *Rheumatol. Int. 14*, pp. 83-84, (1994), Springer-Verlag 1994.

Monier et al., "Growth Factor Activity of Il-6 in the Synovial flud of Patients with Rheumatoid Arthritis", *Clinical and Experimental Rheumatology 12*, pp. 595-602, (1994).

Fukamachi et al., "Interleukin-6 Receptor (Il-6R) Dynamics in Patients with Rheumatoid Arthritis", *Japanese Journal of Inflamation 14*, pp. 489-497, (1994).

Tanabe, M. et al., "Remarkable Elevation of Interleukin 6 and Interleukin 8 Levels in the Bone Morrow Serum of Patients with Rheumatoid Arthritis", *The Journal of Rheumatology 21*, pp. 830-835, (1994).

Mihara et al., "Interleukin-6 (IL-6) Induces the Proliferation of Synovial Fibroblastic Cells in the Presence of Soluble IL-6 Receptor", *British Journal of Rheumatology 34*, pp. 321-325, (1995).

Cicuttini et al., "Serum IL-4, IL-10 and IL-6 Levels in Inflammatory Arthritis", *Rheumatol. Int. 14*, pp. 201-206, (1995), Springer-Verlag 1995.

Scholz et al., "Interleukin 6 in diseases: Cause or Cure?", *Immunopharmacology 31*, pp. 131-150, (1996), 1996 Elsevier Science B.V.

Santo et al., "Differential Effects of IL-6 on Systemic and Central Production of TNF: A Study with IL-6-Deficient Mice", *Cytokine 9*, pp. 300-306, (1997), 1997 Academic Press Limited.

Suzuki et al., "Anti-human Interleukin-6 Receptor Antibody Inhibits Myeloma Growth in vivo", *Eur. J. Immunol. 22*, pp. 1989-1993, (1992) VCH Verlagsgesellschaft mbH, D-3940 Weinheim 19921.

Suzuki et al., "Anti-Murine IL-6 Receptor Antibody Inhibits IL-6 Effects in Vivo", *Immunology Letters 30*, pp. 17-21, (1991), 1991 Elsevier Science Publishers B.V.

Sato et al., "Reshaping a Human Antibody to Inhibit the Interleukin 6-dependent Tumor Cell Growth", Cancer Research 53, pp. 851-856, (1993).

Wijdenes et al., "Interleukin-6 Antobodies in Rheumatoid", *Journal of Interferon Research 14*, pp. 297-298, (1994).

Herve, P. et al., *Immunological Reviews 129*, pp. 31-55, (1992).

Brewer et al., "Penicillamine and hydroxychloriquine in the treatment of severe juvenile rheumatoid arthritis," the New England Journal of Medicine, May 15, 1986, 314(20):1269-1276.

Elliott et al., "Suppression of Fever and the Acute-Phase Response in a Patient with Juvenile chronic Arthritis Treated with Monoclonal Antibody to Tumour Necrosis Factor-α (cA2)," British Journal of Rheumatology, 1997, 36:589-593.

Thompson et al., "Chemokine Receptor CCR4 on CD4+ T Cells in Juvenile Rheumatoid Arthritis Synovial Fluid Defines a Subset of Cells with Increased IL-4:IFN-γ mRNA Ratios," The Journal of Immunology, 2001, 166:6899-6906.

* cited by examiner

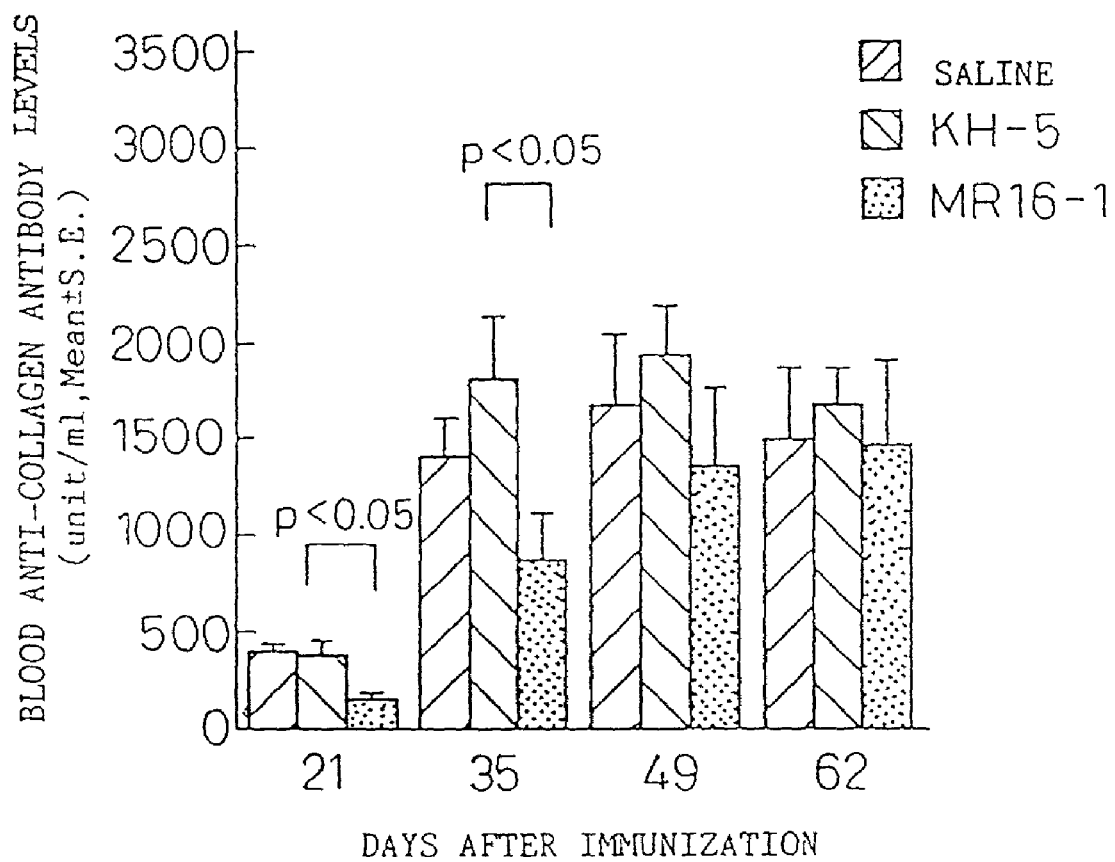

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucletide

<400> SEQUENCE: 1
atattctcta gagagattct                                                  20

<210> SEQ ID NO 2
<211> LENGTH: 11
<212> TYPE: PRT
<213> ORGANISM: Homo sapiens

<400> SEQUENCE: 2

Arg Ala Ser Gln Asp Ile Ser Ser Tyr Leu Asn
  1               5                  10
```

```
<210> SEQ ID NO 3
<211> LENGTH: 7
<212> TYPE: PRT
<213> ORGANISM: Homo sapiens

<400> SEQUENCE: 3

Tyr Thr Ser Arg Leu His Ser
 1               5

<210> SEQ ID NO 4
<211> LENGTH: 9
<212> TYPE: PRT
<213> ORGANISM: Homo sapiens

<400> SEQUENCE: 4

Gln Gln Gly Asn Thr Leu Pro Tyr Thr
 1               5

<210> SEQ ID NO 5
<211> LENGTH: 23
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys
            20

<210> SEQ ID NO 6
<211> LENGTH: 15
<212> TYPE: PRT
<213> ORGANISM: Homo sapiens

<400> SEQUENCE: 6

Trp Tyr Gln Gln Lys Pro Gly Lys Ala Pro Lys Leu Leu Ile Tyr
 1               5                  10                  15

<210> SEQ ID NO 7
<211> LENGTH: 32
<212> TYPE: PRT
<213> ORGANISM: Homo sapiens

<400> SEQUENCE: 7

Gly Val Pro Ser Arg Phe Ser Gly Ser Gly Ser Gly Thr Asp Phe Thr
 1               5                  10                  15

Phe Thr Ile Ser Ser Leu Gln Pro Glu Asp Ile Ala Thr Tyr Tyr Cys
                20                  25                  30

<210> SEQ ID NO 8
<211> LENGTH: 10
<212> TYPE: PRT
<213> ORGANISM: Homo sapiens

<400> SEQUENCE: 8

Phe Gly Gln Gly Thr Lys Val Glu Ile Lys
 1               5                  10

<210> SEQ ID NO 9
<211> LENGTH: 32
<212> TYPE: PRT
<213> ORGANISM: Homo sapiens

<400> SEQUENCE: 9
```

-continued

Gly Val Pro Ser Arg Phe Ser Gly Ser Gly Ser Gly Thr Asp Tyr Thr
 1               5                  10                  15

Phe Thr Ile Ser Ser Leu Gln Pro Glu Asp Ile Ala Thr Tyr Tyr Cys
            20                  25                  30

<210> SEQ ID NO 10
<211> LENGTH: 6
<212> TYPE: PRT
<213> ORGANISM: Homo sapiens

<400> SEQUENCE: 10

Ser Asp His Ala Trp Ser
 1               5

<210> SEQ ID NO 11
<211> LENGTH: 16
<212> TYPE: PRT
<213> ORGANISM: Homo sapiens

<400> SEQUENCE: 11

Tyr Ile Ser Tyr Ser Gly Ile Thr Thr Tyr Asn Pro Ser Leu Lys Ser
 1               5                  10                  15

<210> SEQ ID NO 12
<211> LENGTH: 10
<212> TYPE: PRT
<213> ORGANISM: Homo sapiens

<400> SEQUENCE: 12

Ser Leu Ala Arg Thr Thr Ala Met Asp Tyr
 1               5                  10

<210> SEQ ID NO 13
<211> LENGTH: 30
<212> TYPE: PRT
<213> ORGANISM: Homo sapiens

<400> SEQUENCE: 13

Gln Val Gln Leu Gln Glu Ser Gly Pro Gly Leu Val Arg Pro Ser Gln
 1               5                  10                  15

Thr Leu Ser Leu Thr Cys Thr Val Ser Gly Tyr Ser Ile Thr
            20                  25                  30

<210> SEQ ID NO 14
<211> LENGTH: 14
<212> TYPE: PRT
<213> ORGANISM: Homo sapiens

<400> SEQUENCE: 14

Trp Val Arg Gln Pro Pro Gly Arg Gly Leu Glu Trp Ile Gly
 1               5                  10

<210> SEQ ID NO 15
<211> LENGTH: 32
<212> TYPE: PRT
<213> ORGANISM: Homo sapiens

<400> SEQUENCE: 15

Arg Val Thr Met Leu Arg Asp Thr Ser Lys Asn Gln Phe Ser Leu Arg
 1               5                  10                  15

Leu Ser Ser Val Thr Ala Ala Asp Thr Ala Val Tyr Tyr Cys Ala Arg
            20                  25                  30

<210> SEQ ID NO 16

```
<211> LENGTH: 11
<212> TYPE: PRT
<213> ORGANISM: Homo sapiens

<400> SEQUENCE: 16

Trp Gly Gln Gly Ser Leu Val Thr Val Ser Ser
 1               5                  10
```

CHRONIC RHEUMATOID ARTHRITIS THERAPY CONTAINING IL-6 ANTAGONIST AS EFFECTIVE COMPONENT

The application is a divisional of application Ser. No. 09/233,474, filed Jan. 20, 1999, which is a divisional of application Ser. No. 08/817,084, filed Apr. 7, 1997, now U.S. Pat. No. 5,888,510 issued Mar. 30, 1999, which is a national stage of PCT/JP95/01144, filed Jun. 7, 1995, and a continuation-in-part of Ser. No. 08/971,997, filed Feb. 21, 1997, now abandoned, which is a continuation of Ser. No. 08/268,520, filed Jun. 30, 1994, now abandoned.

TECHNICAL FIELD

The present invention relates to a chronic rheumatoid arthritis therapy or synovial cell growth inhibitor comprising an interleukin-6 antagonist as an effective component.

BACKGROUND ART

Chronic rheumatoid arthritis is a systemic chronic inflammatory disease in which abnormal growth of connective tissue, including synovial tissue, occurs in the joints (Melnyk et al., Arthritis Rheum. 33: 493-500, 1990). The joints of chronic rheumatoid arthritis patients have been shown to have marked growth of synovial cells, formation of a multilayer structure due to abnormal growth of the synovial cells (pannus formation), invasion of the synovial cells into cartilage tissue and bone tissue, vascularization toward the synovial tissue, and infiltration of inflammatory cells such as lymphocytes and macrophages. Mechanisms of onset of chronic rheumatoid arthritis have been reported to be based on such factors as heredity, bacterial infection and the contribution of various cytokines and growth factors, but the overall mechanism of onset has remained unclear.

In recent years, cytokines and growth factors including interleukin-1 (IL-1), interleukin-8 (IL-8), tumor necrosis factor α (TNFα), transforming growth factor β (TGFβ), fibroblast growth factor (FGF) and platelet-derived growth factor (PDGF) have been detected in the synovial membrane and synovial fluid of chronic rheumatoid arthritis patients (Nouri et al., Clin. Exp. Immunol. 55:295-302, 1984; Thornton et al., Clin. Exp. Immunol. 86:79-86, 1991; Saxne, et al., Arthritis Rheum. 31:1041-1045, 1988; Seitz et al., J. Clin. Invest. 87:463-469, 1991; Lafyatis et al., J. Immunol. 143:1142-1148, 1989; Melnyk et al., Arthritis Rheum. 33:493-500, 1990).

It is believed that IL-1, TNFα and PDGF are particularly powerful synovial cell growth factors (Thornton et al., Clin. Exp. Immunol. 86:79-86, 1991; Lafyatis et al., J. Immunol. 143:1142-1148, 1989; Gitter et al., Immunology 66:196-200, 1989). It has also been suggested that stimulation by IL-1 and TNF results in production of interleukin-6 (IL-6) by synovial cells (Ito et al., Arthritis Rheum. 35:1197-1201, 1992).

IL-6 is a cytokine also known as B cell-stimulating factor 2 or interferon β2. IL-6 was discovered as a differentiation factor contributing to activation of B lymphoid cells (Hirano, T. et al., Nature 324, 73-76, 1986), and was later found to be a multifunction cytokine which influences the functioning of a variety of different cell types (Akira, S. et al., Adv. in Immunology 54, 1-78, 1993). Two functionally different membrane molecules are necessary for the induction of IL-6 activities. One of those is IL-6 receptor (IL-6R), an approximately 80 KD molecular weight, which binds specifically to IL-6.

IL-6R exists in a membrane-binding form which is expressed on the cell membrane and penetrates the cell membrane, as well as in the form of soluble IL-6R (sIL-6R) which consists mainly of the extracellular domain. Another protein is gp130 with a molecular weight of approximately 130 KD, which is non-ligand-binding but rather functions to mediate signal transduction. IL-6 and IL-6R form the complex IL-6/IL-6R which in turn binds with another membrane protein gp130, to induce the biological activity of IL-6 to the cell (Taga et al., J. Exp. Med. 196:967, 1987).

It has been reported that the serum or synovial fluid of chronic rheumatoid arthritis patients contains therapies, but since their continuous use induces undesirable side effects such as skin tissue damage and inhibition of adrenal cortex function, drugs with less side effects have been sought.

It is an object of the present invention to provide a novel chronic rheumatoid arthritis therapy without the disadvantages mentioned above. More specifically, the present invention provides a pharmaceutical composition for inhibiting abnormal growth of synovial cells in chronic rheumatoid arthritis, whose effective component is an interleukin-6 antagonist, as well as a pharmaceutical composition for treatment of a chronic rheumatoid arthritis having the same effect.

The present inventors have conducted diligent research on the role of IL-6 on synovial cells from rheumatoid arthritis, during which no growth of chronic rheumatoid arthritis synovial cells was found with IL-6 alone and a factor other than IL-6 was therefore investigated, and this has resulted in completion of the present invention based on the discovery that while IL-6 alone exhibits almost no growth effect on synovial cells, a powerful synovial cell growth effect occurs in the presence of both IL-6 and soluble IL-6R, and further that this synovial cell growth effect is suppressed by addition of an antagonist which inhibits IL-6 activity, such as IL-6 antibody or IL-6R antibody.

In other words, the present invention relates to a pharmaceutical composition for treatment of a chronic rheumatoid arthritis comprising an IL-6 antagonist as the effective component. More specifically, the present invention relates to a pharmaceutical composition for treatment of a chronic rheumatoid arthritis comprising an IL-6 antagonist as the effective component and suppressing abnormal growth of synovial cells. The present invention also relates to a synovial cell growth inhibitor whose effective component is an IL-6 antagonist. excessive amounts of interleukin-6 (IL-6) and soluble IL-6 receptor (sIL-6R) (Houssiau et al., Arthritis Rheum. 31:784-788, 1988; Hirano et al., Eur. J. Immunol. 18:1797-1801, 1988; Yoshioka et al., Japn. J. Rheumatol. in press), and since similar results have also been obtained in rheumatoid arthritis animal models (Takai et al., Arthritis Rheum. 32:594-600, 1989; Leisten et al. Clin. Immunol. Immunopathol. 56: 108-115, 1990), it has been suggested that IL-6 is somehow involved in chronic rheumatoid arthritis.

However, Japanese Unexamined Patent Publication No. 4-89433 discloses that peptides which strongly promote IL-6 production are effective as therapies for chronic rheumatoid arthritis.

Also, Higaki et al. have suggested that synovial cells from chronic rheumatoid arthritis patients have a low growth reaction against IL-6, and that IL-6 thus has an inhibitory function against growth of synovial cells (Clinical Immunology, 22:880-887, 1990). Thus, conflicting reports exist regarding the relationship between IL-6 and chronic rheumatoid arthritis, and the relationship is as yet unclear.

Recently, Wendling et al. have reported that administration of anti-IL-6 antibodies to chronic rheumatoid arthritis patients temporarily alleviates the clinical and biological symptoms, while also increasing IL-6 levels in the serum (J. Rheumatol. 20:259-262, 1993).

These reports provide no data at all about whether IL-6 accelerates growth of chronic rheumatoid arthritis synovial cells or has an inhibitory effect, and thus it is still unknown whether or not IL-6 has a direct effect on synovial cells of chronic rheumatoid arthritis patients.

DISCLOSURE OF THE INVENTION

Anti-inflammatory steroidal agents such as corticosteroids have been used as rheumatoid arthritis

BRIEF DESCRIPTION OF THE DRAWINGS

FIG. 5 is a graph showing serum anti-collagen antibody levels in arthritic mice.

DETAILED DESCRIPTION OF THE INVENTION

Figure 1:
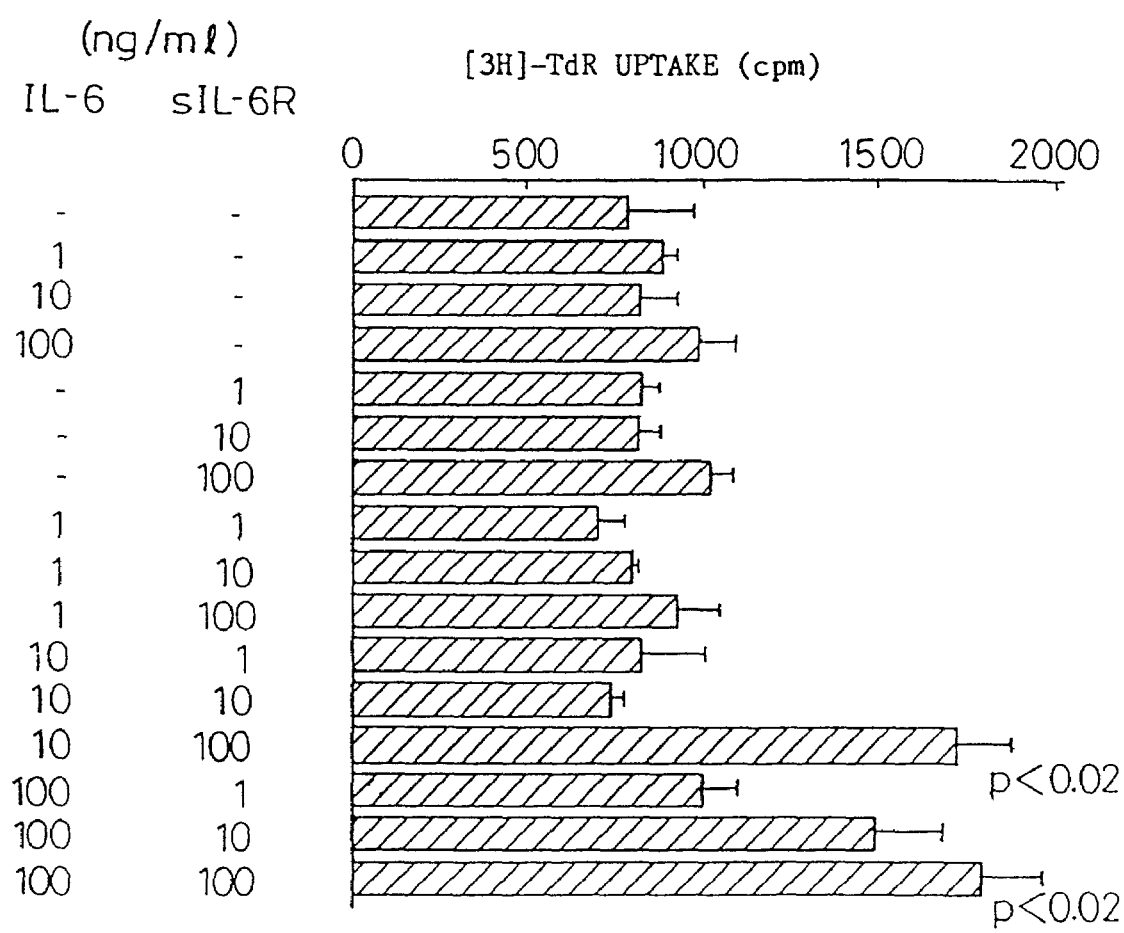
FIG. 1 is a graph showing $^3$H-thymidine uptake into synovial cells in the presence of either IL-6 or sIL-6R alone and in the presence of both IL-6 and sIL-6R.

A pharmaceutical composition for treatment of a chronic rheumatoid arthritis according to the invention is a drug which when administered to chronic rheumatoid arthritis patients suppresses growth of synovial cells in joints and has an alleviating and therapeutic effect on the symptoms.

The IL-6 antagonist used according to the invention may be derived from any source so long as it is a substance which blocks IL-6 signal transfer and inhibits IL-6 biological activity. IL-6 antagonists include IL-6 antibody, IL-6R antibody, gp130 antibody, modified IL-6, antisense IL-6R and partial peptides of IL-6 or IL-6R.

An antibody used as an antagonist according to the invention, such as IL-6 antibody, IL-6R antibody or gp130 antibody, may be of any derivation or type (monoclonal, polyclonal), but monoclonal antibodies derived from mammalian animals are especially preferred. These antibodies bind to IL-6, IL-6R or gp130 to inhibit binding between IL-6 and IL-6R or IL-6R and gp130 and thus block IL-6 signal transduction, inhibiting IL-6 biological activity.

The animal species for the monoclonal antibody-producing cells is not particularly limited so long as it is a mammal, and human antibodies or antibodies derived from a mammal other than human may be used. Monoclonal antibodies derived from a mammal other than human are preferably monoclonal antibodies derived from rabbits or rodents because they are easier to prepare. There is no particular restriction on the rodents, but preferred examples are mice, rats and hamsters.

Examples of such antibodies which are IL-6 antibodies include MH166 (Matsuda et al., Eur. J. Immunol 18:951-956, 1988) and SK2 antibody (Sato et al., Journal for the 21$^{st}$ General Meeting of the Japan Immunology Association, 21:116, 1991). Examples of IL-6R antibodies include PM-1 antibody (deposited on Jul. 12, 1989 at the Patent and Bio-Resource Center, National Institute of Advanced Industrial Science and Technology, Chuo No. 6, 1-1, Higashi 1 chome Tsukuba-shi, Ibaraki-ken 305-5466, Japan, as FERM BP-2998) (Hirata et al., J. Immunol. 143:2900-2906, 1989), AUK12-20 antibody, AUK64-7 antibody and AUK146-15 antibody (Intl. Unexamined Patent Application No. WO92-19759). An example of gp130 antibody is AM64 antibody (Japanese Unexamined Patent Publication 3-219894).

Among these, PM-1 antibody is preferred.

Monoclonal antibodies may be prepared in the following manner which is based on a known technique. That is, IL-6, IL-6R or gp130 is used as the sensitizing antigen for immunization according to a conventional immunizing method, and the resulting immunocytes are then fused with known parent cells by a conventional cell fusion method and monoclonal antibody-producing cells are screened by a conventional screening method to prepare the antibodies.

More specifically, the monoclonal antibodies may be prepared in the following manner. For example, if the sensitizing antigen is human IL-6, the antibodies are obtained using the gene sequence for human IL-6 disclosed by Hirano et al., Nature, 324:73, 1986. The human IL-6 gene sequence is inserted into a publicly expression vector system and used to transform suitable host cells, after which the desired IL-6 protein is purified from the host cells or from the culture supernatant and the purified IL-6 protein is then used as the sensitizing antigen.

In the case of human IL-6R, the IL-6R protein may be obtained by the same method as for human IL-6 described above, using the gene sequence disclosed in European Patent Application No. EP325474. Two types of IL-6R exist, one expressed on the cell membrane and a soluble form (sIL-6R) which is separated from the cell membrane. sIL-6R consists mainly of the extracellular domain of IL-6R which is attached to the cell membrane, and it differs from the membrane-bound IL-6R in that it lacks the transmembrane domain or the transmembrane domain and the intracellular domain.

In the case of human gp130, the gp130 protein may be obtained by the same method as for human IL-6 described above, using the gene sequence disclosed in European Patent Application No. EP411946.

The mammalian animals immunized with the sensitizing antigen are not particularly restricted, but they are preferably selected in consideration of their compatibility with the parent cells used for the cell fusion, and generally mice, rats, hamsters and rabbits may be used.

The immunization of the animals with the sensitizing antigen may be accomplished by a publicly known method. For example, a conventional method involves intraperitoneal or subcutaneous injection of the mammalian animals with the sensitizing antigen. Specifically, the sensitizing antigen is preferably diluted with an equivalent of PBS (Phosphate-Buffered Saline) or physiological saline, suspended and used together with a suitable amount of a conventional adjuvant such as Freund's complete adjuvant if desired, and then administered to the mammalian animals a few times every 4-21 days. An appropriate carrier may also be used for immunization with the sensitizing antigen.

After this immunization and confirmation of increased serum levels of the desired antibody, immunocytes are taken from the mammalian animals and supplied for cell fusion, with especially preferred immunocytes being splenic cells.

The parent cells used for fusion with the above-mentioned immunocytes may be myeloma cells from mammalian animals, and a number of already publicly known cell strains may be suitably used, including P3 (P3x63Ag8.653) (J. Immunol. 123:1548, 1978), p3-U1 (Current Topics in Microbiology and Immunology 81:1-7, 1978), NS-1 (Eur. J. Immunol. 6:511-519, 1976), MPC-11 (Cell, 8:405-415, 1976), SP2/0 (Nature, 276:269-270, 1978), Of (J. Immunol. Meth. 35:1-21, 1980), S194 (J. Exp. Med. 148:313-323, 1978), R210 (Nature, 277:131-133, 1979). The cell fusion of the immunocytes with the myeloma cells may be based on a publicly known method, for example the method of Milstein et al. (Milstein et al., Methods Enzymol. 73:3-46, 1981).

More specifically, the above-mentioned cell fusion is carried out in a conventional nutrient culture in the presence of a cell fusion promoter. The fusion promoter used may be, for example, polyethylene glycol (PEG) or Sendai virus (HVJ), and if desired an aid such as dimethylsulfoxide may also be added to increase the fusion efficiency.

The proportions of the immunocytes and myeloma cells used are preferably a 1- to 10-fold amount of immunocytes with respect to the myeloma cells. The culturing medium used for the cell fusion may be, for example, RPMI1640 culture medium or MEM culture medium which are suitable for growth of myeloma cell strains, or other common culturing media used for such cell culturing, and supplementary serum solutions such as fetal calf serum (FCS) may also be used therewith.

The cell fusion is carried out by thoroughly mixing the prescribed amounts of the immunocytes and the myeloma cells in the culture medium described above, adding a PEG solution preheated to about 37° C., for example with PEG having an average molecular weight of about 1000 to 6000, to the culture medium usually at a concentration of 30 to 60% (w/v), and then mixing to form the desired fused cells (hybridomas). Next, the procedure of gradual addition of a suitable culture medium and centrifugation to remove the supernatant is repeated, to accomplish removal of the cell fusing agent, etc. which is unfavorable for growth of the hybridomas.

Suitable hybridomas are selected by culturing in a normal selective culture medium, such as HAT culture medium (containing hypoxanthine, aminopterin and thymine). The culturing in the HAT culture medium is continued for a given time, usually a few days to a few weeks, sufficient for death of the cells other than the hybridomas (non-fused cells). Next, normal limited dilution is carried out, and the hybridomas producing the desired antibodies are subjected to masking and monocloning.

The monoclonal antibody-producing hybridomas prepared in this manner may be subcultured in a common culture solution and they may also be placed in liquid nitrogen for long-term storage.

In order to acquire the monoclonal antibodies from the hybridomas, the hybridomas are cultured according to a conventional method after which the culture supernatant is recovered, or else a method is used whereby the hybridomas are injected to a compatible mammalian animal, grown, and the ascites fluid is obtained. The former method is suited for obtaining high purity antibodies, while the latter method is suited for mass production of the antibodies.

The monoclonal antibodies obtained by these methods may then be purified to a high degree using conventional purification means, such as salting-out, gel filtration, affinity chromatography or the like.

The monoclonal antibodies prepared in this manner may then be checked for high sensitivity and high purity recognition of the antigen by common immunological means such as radioimmunoassay (RIA), enzyme-linked immunoassay, (EIA, ELISA), the fluorescent antibody technique (immunofluorescence analysis), etc.

The monoclonal antibodies used according to the invention are not limited to monoclonal antibodies produced by hybridomas, and they may be ones which have been artificially modified for the purpose of lowering the heteroantigenicity against humans. For example, a chimeric antibody may be used which consists of the variable region of a monoclonal antibody of a mammalian animal other than human, such as a mouse, and the constant region of a human antibody, and such a chimeric antibody may be produced by a known chimeric antibody-producing method, particularly a gene recombination technique.

Reshaped human antibodies may also be used according to the invention. These are prepared by using the complementary determinant region of a mouse or other non-human mammalian animal antibody to replace the complementary determinant region of a human antibody, and conventional gene recombination methods therefor are well-known. One of the known methods may be used to obtain a reshaped human antibody which is useful according to the invention. A preferred example of such a reshaped human antibody is hPM-1 (see Intl. Unexamined Patent Application No. WO92-19759).

When necessary, amino acids of the framework (FR) region of the variable region of an antibody may be substituted so that the complementary determinant region of the reshaped human antibody forms a suitable antibody binding site (Sato et al., Cancer Res. 53:851-856, 1993). In addition, the object stated above may also be achieved by constructing a gene coding for an antibody fragment which binds to the antigen to inhibit IL-6 activity, such as Fab or Fv, or a single chain Fv (scFv) wherein the Fv of the H and L chains are attached via an appropriate linker, and using it for expression in appropriate host cells (see, for example, Bird et al., TIBTECH, 9:132-137, 1991; Huston et al., Proc. Natl. Acad. Sci. USA, 85:5879-5883, 1988).

Modified IL-6 used according to the invention may be the one disclosed by Brakenhoff et al, J. Biol. Chem. 269:86-93, 1994 or Savino et al., EMBO J. 13:1357-1367, 1994.

The modified IL-6 used may be obtained by introducing a mutation such as a substitution, deletion or insertion into the IL-6 amino acid sequence to maintain the binding activity with IL-6R while eliminating the IL-6 signal transfer function. The IL-6 source may be from any animal species so long as it has the aforementioned properties, but in terms of antigenicity, a human derived one is preferably used.

Specifically, the secondary structure of the IL-6 amino acid sequence may be predicted using a publicly known molecular modeling program such as WHATIF (Vriend et al., J. Mol. Graphics, 8:52-56, 1990), whereby the influence of mutated amino-acid residues on the entire structure may also be evaluated. After determining appropriate mutated amino acid residues, a vector containing the nucleotide sequence coding for the human IL-6 gene is used as a template for introduction of the mutation by the conventionally employed PCR (polymerase chain reaction) method, to obtain a gene coding for the modified IL-6. This is then incorporated into a suitable expression vector if necessary and expressed in E. coli cells or mammalian cells, and then used either while in the culture supernatant or after isolation and purification by conventional methods, to evaluate the binding activity for IL-6R and the neutralized IL-6 signal transfer activity.

An IL-6 partial peptide or IL-6R partial peptide used according to the present invention may have any sequence so long as it binds to IL-6R or IL-6, respectively, and has no IL-6 activity transfer function. IL-6 partial peptides and IL-6R partial peptides are described in U.S. Patent Publication No. US5210075. An IL-6 antisense oligonucleotide is described in Japanese Patent Application No. 5-300338.

Figure 6A:
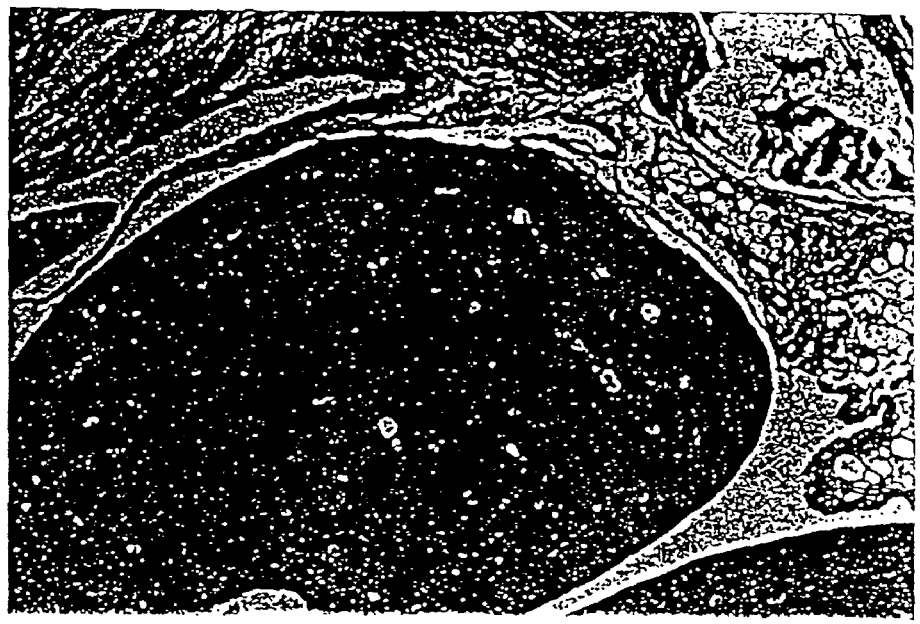
FIG. 6 is a photograph of histopathological examination of hind paw joint of a collagen-arthritis mouse. (a) is a photograph from a mouse in an IL-6 receptor antibody-administered group, and (b) is from a mouse in a control antibody-administered group. In the IL-6 receptor antibody-administered group, invasion of granulation tissue into the cartilage and bone (chronic proliferative synovitis) was clearly suppressed.
Figure 6B:

A pharmaceutical composition for treatment of chronic rheumatoid arthritis whose effective component is an IL-6 antagonist according to the invention is effective for treatment of chronic rheumatoid arthritis if it blocks IL-6 signal transduction and suppresses abnormal growth of synovial cells induced by IL-6, which are implicated in the disease. Example 1 demonstrates the in vitro growth suppressing effect on rheumatic patient-derived synovial cells. In Example 2, IL-6 receptor antibody was administered to mice arthritic models immunized with type II collagen, and the relevant data demonstrates (1) suppression of onset of arthritis on the basis of an arthritis index (FIG. 4), (2) suppression of anti-type II collagen antibody production in the blood of collagen-immunized mice (FIG. 5) and (3) suppression of granulation tissue invasion into cartilage and bone (chronic proliferative synovitis) in the hind paw joints of mice arthritic models administered IL-6 receptor antibody (FIG. 6).

In regard to (1) and (2) above, the results confirmed a suppressing effect by IL-6 receptor antibody, especially initially, on onset of arthritis in the mice models. The results of (3) demonstrated that invasion of granulation tissue into the cartilage and bone tissue is suppressed, and this supports the results obtained in Example 1 (in vitro inhibition of synovial cell growth).

The experimental results of (1) and (2) indicate that the pharmaceutical composition for treatment of chronic rheumatoid arthritis of the present invention has an excellent initial effect on rheumatoid arthritis.

The pharmaceutical composition for treatment of chronic rheumatoid arthritis of the invention is preferably administered parenterally, for example by intravenous, intramuscular, intraperitoneal or subcutaneous injection, either systemically or locally. Also, it may be in the form of a medical formulation kit together with at least one type of medical carrier or diluent.

The dosage of the pharmaceutical composition for treatment of chronic rheumatoid arthritis of the invention when administered to humans will differ depending on pathological condition and age of the patient, and the mode of administration, and thus suitable and appropriate doses must be selected. As an example, a maximum of 4 divided doses in the range of about 1 to 1000 mg/patient may be selected. However, the pharmaceutical composition for treatment of rheumatoid arthritis of the invention is not limited to these dosages.

The pharmaceutical composition for treatment of rheumatoid arthritis of the invention may be formulated according to conventional methods. For example, an injection formulation is prepared by dissolving the purified IL-6 antagonist in a solvent such as physiological saline or a buffer solution and then adding an adsorption inhibitor such as Tween 80, gelatin, human serum albumin (HSA) or the like, and the mixture may be lyophilized prior to use for solution reconstitution. The excipient used for lyophilization may be a sugar alcohol such as mannitol or glucose, or a saccharide.

EXAMPLES

The present invention will now be explained in more detail by way of the following examples, reference examples and experimental examples, with the understanding that the invention is in no way restricted thereto.

Reference Example 1

Preparation of Human Soluble IL-6 Receptor

Soluble IL-6R was prepared (Yasukawa et al., J. Biochem. 108:673-676, 1990) by the PCR (polymerase chain reaction) method using plasmid pBSF2R.236 containing cDNA coding for human IL-6 receptor (IL-6R) obtained according to the method of Yamasaki et al. (Science, 241:825-828, 1988).

The aforementioned plasmid pBSF2R.236 was digested with restriction enzyme Sphl to obtain an IL6R cDNA fragment which was then inserted into mp18 (Amersham Co.). The synthetic oligoprimer (SEQ ID NO: 1) ATATTCTCTA-GAGAGATTCT designed for introduction of a stop codon in IL-6R cDNA was used to introduce a mutation in the IL-6R cDNA by the PCR method using an Invitro Mutagenesis System (Amersham Co.). This procedure resulted in introduction of a stop codon at the position of amino acid 345 to obtain cDNA coding for soluble IL-6R (sIL -6R).

In order to express the sIL-6R cDNA in CHO cells, the aforementioned sIL-6R cDNA cut with HindIII-SalI was inserted into plasmid pECEdhfr (Clauser et al., Cell, 45:721-735, 1986) which had cDNA coding for dihydrofolate reductase (dhfr) inserted at the restriction enzyme PvuI cleavage site, to obtain the CHO cell expression plasmid pECEdhfr344.

A 10 μg of plasmid pECEdhfr344 was used for transfection of the dhfr-CHO cell line DXB-11 (Urland et al., Proc. Natl. Acad. Sci. USA 77, 4216-4220, 1980) by the calcium phosphate precipitation method (Chen et al., Mol. Cell. Biol. 7:2745-2751, 1987).

The transfected CHO cells were cultured for 3 weeks in a nucleoside-free αMEM selective culture medium containing 1 mM glutamine, 10% dialyzed Fetal Calf Serum (FCS), 100 U/ml penicillin and 100 μg/ml streptomycin. The selected CHO cells were screened by the limiting dilution method, and a single monoclonal CHO cell line was obtained. The CHO cell clone was amplified in 20 nM to 200 nM concentration methotrexate (MTX), to obtain the human sIL-6R-producing CHO cell line 5E27.

The CHO cell line 5E27 was cultured in Iscove's modified Dulbecco's medium (IMDM, product of Gibco Co.) containing 5% FCS, the culture supernatant was recovered, and the sIL-6R concentration in the culture supernatant was measured by the ELISA (Enzyme-Linked Immunosorbent Assay) method according to the common procedure.

Reference Example 2

Preparation of Human IL-6 Antibody

Human IL-6 antibody was prepared according to the method of Matsuda et al. (Eur. J. Immunol. 18:951-956, 1988).

BALB/c mice were immunized with 10 μg of recombinant IL-6 (Hirano et al., Immunol. Lett., 17:41, 1988) together with Freund's complete adjuvant, and this was continued once a week until anti-IL-6 antibodies were detected in the blood serum.

Immunocytes were extracted from the local lymph nodes, and polyethylene glycol 1500 was used for fusion with the myeloma cell line P3U1. Hybridomas were selected according to the method of Oi et al. (Selective Methods in Cellular Immunology, W. H. Freeman and Co., San Francisco, 351, 1980) using HAT culture medium, and a human IL-6 antibody-producing hybridoma line was established. The human IL-6 antibody-producing hybridoma was subjected to IL-6 binding assay in the following manner.

Specifically, a soft polyvinyl 96-well microplate (product of Dynatech Laboratories, Inc., Alexandria, Va.) was coated overnight with 100 μl of goat anti-mouse Ig antibody (10 μl/ml, product of Cooper Biomedical, Inc., Malvern, Pa.) in a 0.1M carbonate-hydrogen carbonate buffer solution (pH 9.6) at 4° C. The plate was then treated for 2 hours at room temperature with PBS containing 100 μl of 1% bovine serum albumin (BSA). After washing with PBS, 100 μl of hybridoma culture supernatant was added to each well, and incubation was conducted overnight at 4° C.

The plates were then washed and $^{125}$I-labelled recombinant IL-6 was added to each well to 2000 cpm/0.5 ng/well, and after washing, the radioactivity of each well was measured with a gamma counter (Beckman Gamma 9000, Beckman Instruments, Fullerton, Calif.). Of 216 hybridoma clones, 32 hybridoma clones were positive for the IL-6 binding assay. Among these clones there was finally obtained the stable clone MH166.BSF2. The IL-6 antibody MH166 produced by this hybridoma has an IgG1K subtype.

The IL-6-dependent mouse hybridoma cell line MH60.BSF2 (Matsuda et al., Eur. J. Immunol. 18:951-956, 1988) was then used to determine the neutralizing activity of MH166 antibody on growth of the hybridoma. MH60.BSF2 cells were dispensed at an amount of $1\times10^4$/200 μl/well, a sample containing MH166 antibody was added thereto, culture was performed for 48 hours, and 15.1 Ci/mmol of $^3$H-thymidine (New England Nuclear, Boston Mass.) was added, after which culture was continued for 6 hours.

The cells were placed on glass filter paper and treated with an automatic harvester (Labo Mash Science Co., Tokyo, Japan). Rabbit anti-IL-6 antibody was used as a control. As a result, MH166 antibody inhibited uptake of $^3$H-thymidine by the MH60.BSF2 cells in a dose-dependent manner. This demonstrated that MH166 antibody neutralizes IL-6 activity.

Reference Example 3

Preparation of Human IL-6 Receptor Antibody

Anti-IL-6R antibody MT18 constructed by the method of Hirata et al. (J. Immunol., 143:2900-2906, 1989) was bound to Sepharose 4B (product of Pharmacia Fine Chemicals, Piscataway, N.J.) activated with CNBr, according to the accompanying instructions, and the bound complex was used to purify IL-6R (Yamasaki et al., Science 241:825-828, 1988).

The human myeloma cell line U266 was solubilized with 1 mM p-paraaminophenylmethane sulfonylfluoride hydrochloride (product of Wako Chemicals) containing 1% digitonin (product of Wako Chemicals), 10 mm triethanolamine (pH 7.8) and 0.15M NaCl (digitonin buffer solution), and mixed with MT18 antibody bound to Sepharose 4B beads. The beads were then washed 6 times with digitonin buffer solution to obtain partially purified IL-6R for immunization.

BALB/c mice were immunized 4 times every 10 days with the partially purified IL-6R obtained from $3\times10^9$ U266 cells, and then hybridomas were prepared by conventional methods. The culture supernatants of the hybridomas from the growth-positive wells were examined for IL-6 binding activity by the following method. After labelling $5\times10^7$ U266 cells with $^{35}$S-methionine (2.5 mCi) they were solubilized with the aforementioned digitonin buffer solution. The solubilized U266 cells were mixed with a 0.04 ml of MT18 antibody bound to Sepharose 4B beads, and after washing 6 times with digitonin buffer solution, the $^{35}$S-methionine-labelled IL-6R was washed off with 0.25 ml of digitonin buffer solution (pH 3.4) and neutralized with 0.025 ml of 1M Tris (pH 7.4).

A 0.05 ml of the hybridoma culture supernatant was mixed with 0.01 ml of Protein G Sepharose (product of Pharmacia). After washing, the Sepharose was incubated with 0.005 ml of the $^{35}$S-labelled IL-6R solution prepared earlier. The immunoprecipitated substance was analyzed by SDS-PAGE, and the hybridoma culture supernatants reacting with IL-6R were examined. As a result, a reaction-positive hybridoma clone PM-1 was established. The IL-6R antibody PM-1 produced by hybridoma PM-1 has an IgG1K subtype.

The inhibiting activity of the antibody produced by hybridoma PM-1 against binding of IL-6 to human IL-6R was investigated using the human myeloma cell line U266. Human recombinant IL-6 was prepared with *E. coli* (Hirano et al., Immunol. Lett., 17:41, 1988) and $^{125}$I-labelled with Bolton-Hunter reagent (New England Nuclear, Boston, Mass.) (Taga et al., J. Exp. Med. 166:967, 1987).

$4\times10^5$ U266 cells were cultured at room temperature in the presence of a 100-fold excess of non-labelled IL-6 for one hour, together with 70% (v/v) of hybridoma PM-1 culture supernatant and 14000 cpm of $^{125}$I-labelled IL-6. A 70 μl sample was overlaid onto 300 μl of FCS placed in a 400 μl microfuge polyethylene tube, and after centrifugation the radioactivity on the cells was measured.

As a result it was demonstrated that the antibodies produced by hybridoma PM-1 inhibited binding of IL-6 to IL-6R.

Reference Example 4

Preparation of Mouse IL-6 Receptor Antibody

Monoclonal antibodies against mouse IL-6 receptor were prepared by the method described in Japanese Patent Application No. 6-134617.

Following the method of Saito et al. (J. Immunol., 147, 168-173, 1993), CHO cells producing mouse soluble IL-6 receptor were cultured in IMDM medium containing 10% FCS, and the mouse soluble IL-6 receptor was purified from the culture supernatant using the mouse soluble IL-6 receptor antibody RS12 (see ibid. Saito et al.) and an affinity column immobilizing Affigel 10 gel (Biorad).

A 50 μg of the obtained mouse soluble IL-6 receptor was mixed with Freund's complete adjuvant and intraperitoneally injected into wistar rats (Nihon Charles River Co.). Booster immunizations were given with Freund's incomplete adjuvant after 2 weeks. On the 45th day the rats were butchered, and about $2\times10^8$ splenic cells thereof were used for cell fusion with $1\times10^7$ mouse P3U1 myeloma cells by a conventional method utilizing 50% PEG1500 (Berlinger Mannheim), after which the hybridomas were screened with HAT medium.

After adding the hybridoma culture supernatants to an immunoplate coated with rabbit anti-rat IgG antibody (Cappel Co.), mouse soluble IL-6 receptor was reacted therewith and the hybridomas producing antibodies against mouse soluble IL-6 receptor were screened by the ELISA method using rabbit anti-mouse IL-6 receptor antibody and alkali phosphatase-labelled sheep anti-rabbit IgG. The hybridoma clones in which antibody production was confirmed were subjected to subscreening twice to obtain a single hybridoma clone. This clone was named MR16-1.

The neutralizing activity of the antibody produced by this hybridoma against mouse IL-6 signal transduction was investigated by incorporation of $^3$H-thymidine using MH60.BSF2 cells (Matsuda et al., J. Immunol. 18, 951-956, 1988), MH60.BSF2 cells were added to a 96-well plate to 1×10⁴ cells/200 µl/well, and then mouse IL-6 (10 pg/ml) and MR16-I antibody or RS12 antibody were added to 12.3-1000 ng/ml prior to culturing at 37° C., in 5% $CO_2$ for 44 hours, after which $^3$H-thymidine (1 µCi/well) was added and the uptake after 4 hours was measured. As a result, MR16-1 antibody was found to inhibit uptake of $^3$H-thymidine by MH60.BSF2 cells.

Experiment 1

Establishment of Chronic Rheumatoid Arthritis-derived Synovial Cell Line (1) Preparation of synovial cells Synovial tissue was obtained during surgical operation on the joint of a chronic rheumatoid arthritis patient. The synovial tissue was minced with scissors and then subjected to enzymatic dissociation by incubation for one hour at 37° C. with 5 mg/ml of TYPE I collagenase (product of Sigma Chemical Co.) and 0.15 mg/ml of bovine pancreatic DNase (product of Sigma Chemical Co.) in IMDM (Iscove's modified Dulbecco's medium), and passed through a mesh to obtain single cells. These obtained cells were then cultured overnight in a culture flask using IMDM containing 5% FCS, after which the non-adherent cells were removed to obtain the synovial cells. The synovial cells were passaged 3 to 6 times and used for the following experiment.

(2) IL-6 production by synovial cells

The synovial cells obtained as described above were suspended in IMDM culture medium containing 5% FCS (product of Hyclone Laboratories Inc.), 10 U/ml of penicillin G and 100 µg/ml streptomycin to an amount of 3×10³ cells/well, and were then cultured in 96-well microtiter plate (product of Falcon Co.), which human interleukin-1β (IL-1β), human tumor necrosis factor α (TNFα), human platelet-derived growth factor (PDGF)AB and human basic fibroblast growth factor (bFGF) were added to concentrations of 0.01 or 0.1, 0.1 or 1, 1 or 10 and 1 or 10 ng/ml, respectively, and upon culturing at 37° C. for 72 hours the culture supernatants were collected.

A 100 µl of anti-human IL-6 antibody MH166 (1 µg/ml) was added to a 96-well ELISA plate (Immunoplate: product of Nunc Co.) and incubated at 4° C. for 24 hours. Each well was subsequently washed with PBS containing 0.05% Tween 20, and blocked at 4° C. overnight with PBS containing 1% BSA. The culture supernatants obtained previously were then diluted with PBS containing 1% BSA, added to the wells, and then incubated at room temperature for 2 hours. After washing with PBS containing 0.05% Tween20, 2.5 µg/ml of rabbit polyclonal anti-human IL-6 antibody purified with a 100 µl protein A column (product of Pharmacia) was added.

After incubating at room temperature for 2 hours, the rabbit polyclonal anti-IL-6 antibody binding to IL-6 in the culture supernatants was reacted with alkali phosphatase-bound anti-rabbit IgG antibody (product of Tago Co.). And then 1 mg/ml of Sigma104 alkali phosphatase substrate (product of Sigma Co.) was added according to the attached instructions and the absorbance at 405-600 nm was measured with an MPR A4 microplate reader (product of Tosoh Co.).

Calibration curves were prepared for the recombinant IL-6 during each assay for conversion of the absorbance OD values to human IL-6 concentrations. The results are given in Table 1.

TABLE 1

| Augmented IL-6 production from synovial cell | | |
|---|---|---|
| Treatment (ng/ml) | | IL-6 (ng/ml) |
| Untreated | | 0.096 ± 0.012 |
| IL-1β | 0.01 | 6.743 ± 0.178 |
| | 0.1 | 17.707 ± 0.259 |
| TNFα | 0.1 | 0.575 ± 0.008 |
| | 1 | 1.688 ± 0.034 |
| PDGF-AB | 1 | 0.163 ± 0.035 |
| | 10 | 0.165 ± 0.016 |
| bFGF | 1 | 0.181 ± 0.009 |
| | 10 | 0.230 ± 0.019 |

Note: The synovial cells were cultured for 3 days with IL-1β, TNFα, PDGF-AB or bFGF. After culture, the IL-6 concentrations of the supernatants were measured by ELISA.

The results demonstrated that IL-1β strongly promotes IL-6 production by synovial cells.

Example 1

(1) The synovial cells obtained in Experiment 1 (3×10³/well) were suspended in IMDM culture medium containing 5% FCS (product of Hyclone Laboratories, Inc.), 10 U/ml of penicillin G and 100 µg/ml of streptomycin and were then added into a 96-well microtiter plate (#3072, product of Falcon Co.) and cultured for 5 days in the presence of various concentrations of IL-6 or sIL-6 alone, or in the presence of both IL-6 and sIL-6R. At 72 hours after starting the culturing, $^3$H-thymidine (product of Amersham International plc) was added to each well to 1 µCi/well, and after the culturing was completed the radioactivity in the cells was measured with a scintillation counter. The results are shown in FIG. 1.

As a result, the $^3$H-thymidine uptake of the synovial cells was low with IL-6 or sIL-6R alone, and no growth of synovial cells was observed. In contrast, in the presence of at least a 10 ng/ml concentration of IL-6 and 100 ng/ml concentration of sIL-6R, significant uptake of $^H$-thymidine was observed compared to the control group. Thus, while virtually no growth effect on synovial cells was exhibited with IL-6 alone, in the presence of both IL-6 and sIL-6R a powerful synovial cell growth effect was clearly produced.

Figure 2:
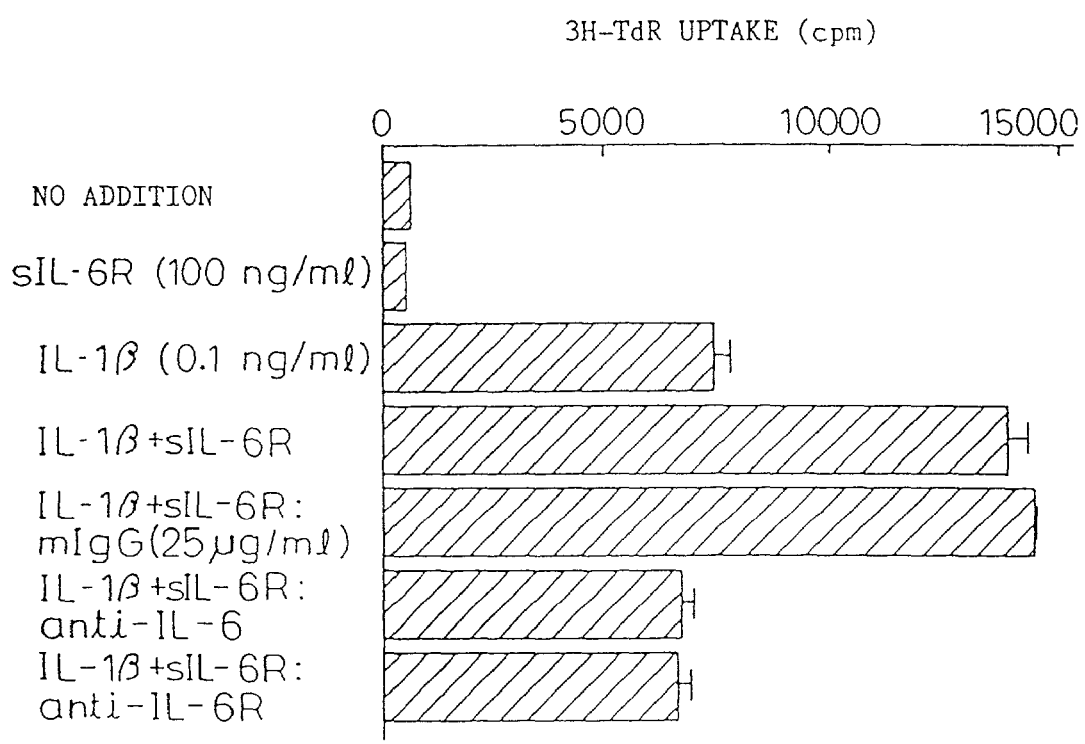
FIG. 2 is a graph showing the effect of IL-6 antibody or IL-6R antibody on $^3$H-thymidine uptake into synovial cells in the presence of both IL-1β and sIL-6R.

(2) Synovial cells (3×10³/well) were cultured in the presence of a sufficient amount of IL-β to produce IL-6 (0.1 ng/ml), 100 ng/ml of sIL-6R and 25 µg/ml of IL-6 antibody or 25 µg/ml of IL-6R antibody. At 72 hours after the start of culturing, $^3$H-thymidine was added to each well to 1 µCi/well, and after the culture was completed the radioactivity in the cells was measured with a scintillation counter. The results are shown in FIG. 2. Addition of IL-6 antibody or IL-6R antibody completely suppressed the growth of synovial cells augmented by sIL-6R.

Figure 3:
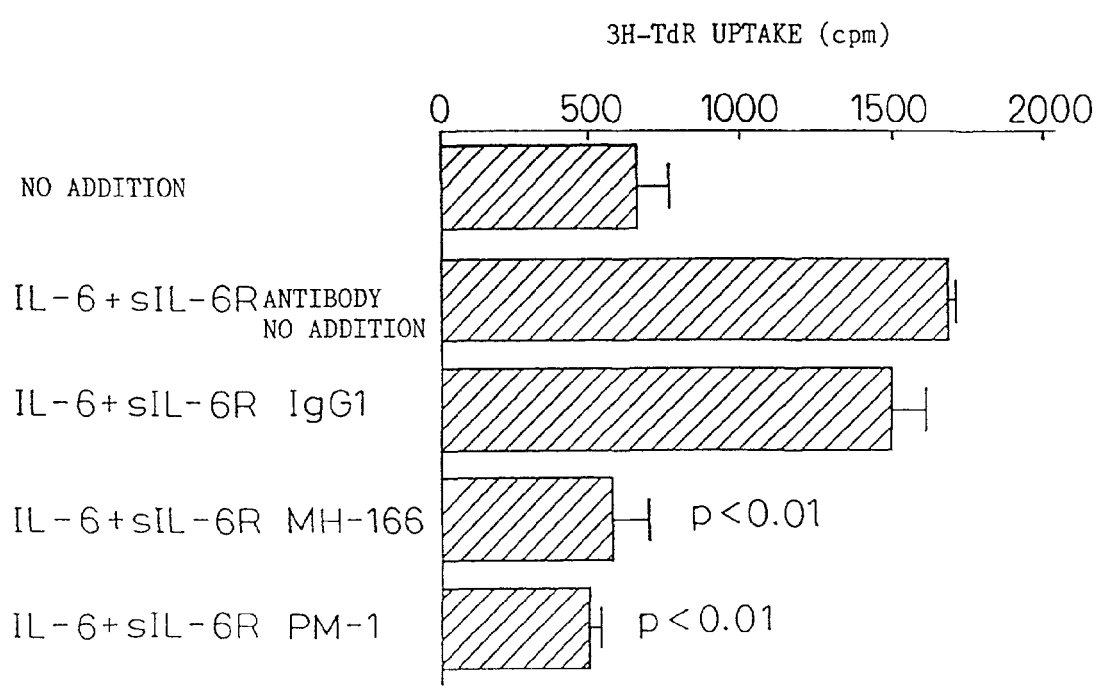
FIG. 3 is a graph showing the effect of IL-6 antibody or IL-6R antibody on $^3$H-thymidine uptake into synovial cells in the presence of both IL-6 and sIL-6R.

(3) Synovial cells (3×10³/well) were cultured in the presence of 100 ng/ml of IL-6 (product of Genzyme Co.), 100 ng/ml of sIL-6R and 25 µg/ml of IL-6 antibody or IL-6R antibody, which were obtained in the above-mentioned Reference Examples. At 72 hours after the start of culture, $^3$H-thymidine was added to each well to 1 µCi/well, and after the culture was completed, the radioactivity in the cells was measured with a scintillation counter. The results are shown in FIG. 3. Addition of IL-6 antibody or IL-6R antibody completely suppressed the growth of synovial cells augmented by sIL-6R.

Example 2

The suppressing effect of IL-6 receptor antibody on onset of arthritis was investigated using a mouse arthritis model.

A bovine type II collagen solution (Collagen Technology Research Group) (4 mg/ml) dissolved in a 0.1 N aqueous acetic acid solution and complete adjuvant H37Ra (DIFCO) were mixed in equivalent amounts, to prepare an adjuvant. A 100 μl of the adjuvant was subcutaneously injected at the base of tail of 8- to 9-week-old female DBA/1J mice (Charles River Japan). An additional 100 μl was injected 20 days later under the dorsal skin to induce arthritis.

Mouse IL-6 receptor antibody MR16-1 was intravenously administered at 2 mg per mouse upon first collagen sensitization, and each mouse was subcutaneously injected with an additional 0.5 mg (n=5) each week thereafter for 7 weeks. As a control, anti-DNP antibody KH-5 (Chugai Seiyaku) of the same isotype was used (n=5).

The severity of arthritis was evaluated based on an arthritis index. The evaluation was based on a 4 point scale for each limb, for a total of 16 points per individual. The evaluation standard was as follows.

0.5: Erythema observed at one site of joint.
1: Erythema observed at two sites of joint, or redness but no swelling of dorsa.
2: Moderate swelling observed.
3: Severe swelling of pedal dorsa, but not reaching all of the digits.
4: Severe swelling of pedal dorsa and digits.

Figure 4:
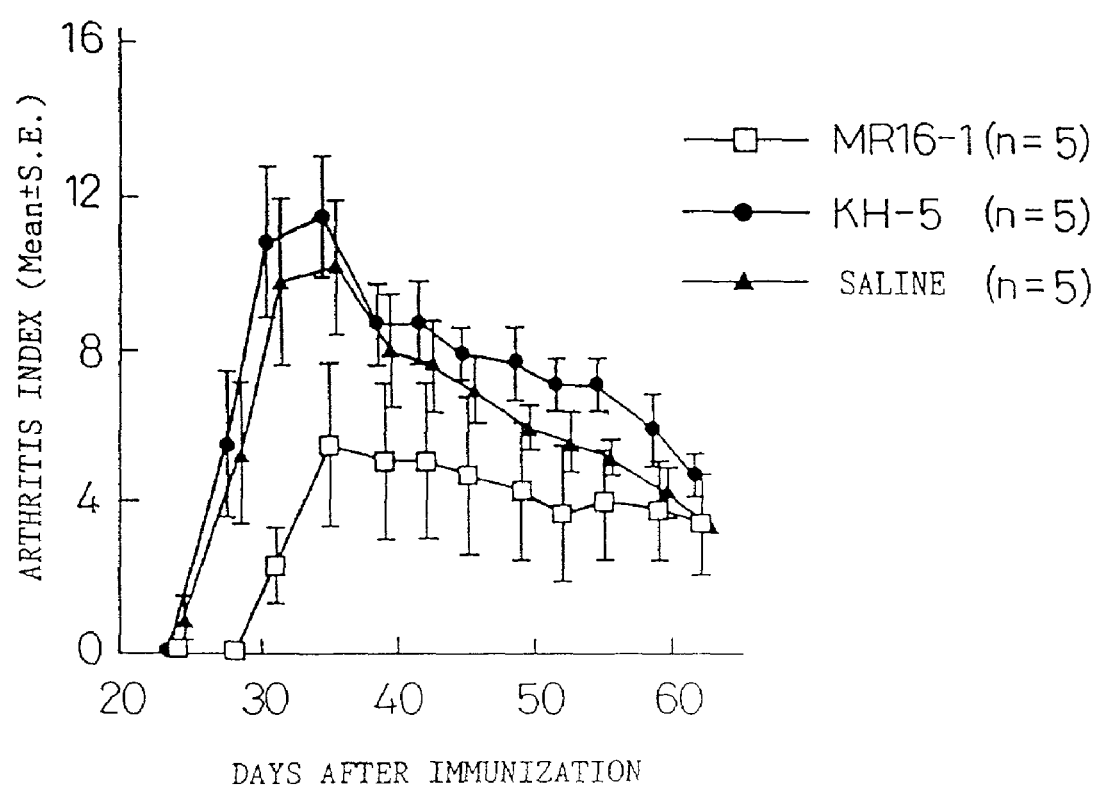
FIG. 4 is a graph showing the suppressive effect of IL-6R antibody on the onset of mouse collagen-induced arthritis models.

The results are shown in FIG. 4. Onset of arthritis from early stage arthritis was clearly suppressed in the IL-6 receptor antibody-administered group, compared to the control antibody-administered group.

On the other hand, the results of measurement of the anti-type II collage antibody titer in the mouse blood showed a significant reduction from early stage arthritis in the IL-6 receptor antibody-administered group compared to the control antibody-administered group (FIG. 5).

The mice were sacrificed on the 35th day after collagen immunization, and the hind legs were fixed with 20% formalin. They were then subjected to demineralization in an EDTA solution (pH 7.6) and dewatering with alcohol. They were subsequently wrapped in paraffin and cut to 2 μm thick sections. The sections were stained with hematoxylin and eosin and observed under 125× magnification (FIG. 6). As a result, invasion of granulation tissue into the cartilage and bone, i.e. chronic proliferative synovitis was suppressed in the IL-6 receptor antibody-administered group compared to the control antibody-administered group.

IL-6 is a cytokine which induces differentiation of B cells into antibody-producing cells. IL-6 also promotes proliferation of synovial cells in the presence of IL-6 receptor. Since in mouse collagen arthritis models, anti-IL-6 receptor antibody significantly suppressed anti-type II collagen antibody titers on the 21st and 35th days after collagen sensitization, compared to the control antibody-administered group, it is believed that the antibody production inhibition by anti-IL-6 receptor antibody is one factor responsible for the suppressing effect on arthritis. Moreover, although no suppression of antibody production was observed from the 49th day after collagen sensitization, the fact that an adequate suppressing effect on onset of arthritis was exhibited even during this period, and that HE staining of tissue surrounding the tarsal bone showed suppressed invasion of granulation tissue into the cartilage and bone of the anti-IL-6 receptor antibody-administered group compared to the control group, the synovial growth-suppressing effect is also believed to contribute to the arthritis-inhibiting effect.

INDUSTRIAL APPLICABILITY

Synovial cells from chronic rheumatoid arthritis patients proliferate in the presence of both IL-6 and sIL-6R. The fact that synovial fluid of chronic rheumatoid arthritis patients contains a sufficient amount of IL-6 and sIL-6R to induce growth of synovial cells suggests that signal transduction by IL-6 is involved in abnormal growth of synovial cells in chronic rheumatoid arthritis.

It has thus been conclusively demonstrated that a chronic rheumatoid arthritis therapy whose effective component is an IL-6 antagonist according to the present invention suppresses growth of synovial cells in chronic rheumatoid arthritis patients in the presence of IL-6 and sIL-6R, and thus has a therapeutic effect against chronic rheumatoid arthritis. Consequently, the IL-6 antagonist of the invention is useful as a therapeutic agent for chronic rheumatoid arthritis in which abnormal growth of synovial cells occurs.

The invention claimed is:

1. A method for inhibiting synovial cell growth, comprising administering to a patient in need thereof a pharmaceutical composition comprising reshaped human antibody hPM-1 and a physiologically acceptable carrier.

2. A method of treating chronic rheumatoid arthritis, comprising administering to a patient in need thereof a pharmaceutical composition comprising reshaped human antibody hPM-1 and a physiologically acceptable carrier.

3. The method according to claim 2, wherein the antibody suppresses abnormal growth of synovial cells.

* * * * *